(12) United States Patent
Ren et al.

(10) Patent No.: US 9,555,214 B2
(45) Date of Patent: Jan. 31, 2017

(54) EXPANDABLE INTRODUCER SHEATH AND RELATED METHODS (71) Applicant: RG Innovation, LLC, Maple Grove, MN (US)

(72) Inventors: Brooke Ren, Maple Grove, MN (US); Jason Galdonik, Minneapolis, MN (US)

(73) Assignee: RG Innovation, LLC, Maple Grove, MN (US)

(*) Notice: Subject to any disclaimer, the term of this patent is extended or adjusted under 35 U.S.C. 154(b) by 0 days.

(21) Appl. No.: 14/568,798

(22) Filed: Dec. 12, 2014

(65) Prior Publication Data

US 2015/0165158 A1   Jun. 18, 2015

Related U.S. Application Data

(60) Provisional application No. 61/915,108, filed on Dec. 12, 2013.

(51) Int. Cl.
*A61M 25/00* (2006.01)
*A61M 25/06* (2006.01)

(52) U.S. Cl.
CPC ...... *A61M 25/0023* (2013.01); *A61M 25/0662* (2013.01); *A61M 2025/0024* (2013.01)

(58) Field of Classification Search
CPC ............. A61M 25/0023; A61M 2025/0025; A61M 25/0662; A61M 2025/0687; A61M 2025/0024; A61B 17/3415; A61B 17/3421; A61B 17/3439; A61B 17/3431
USPC ................. 604/264, 104–107; 606/191–194
See application file for complete search history.

(56) References Cited

U.S. PATENT DOCUMENTS

| 6,692,462 B2* | 2/2004 | Mackenzie | ........ A61B 17/3415 604/104 |
| 7,575,569 B2* | 8/2009 | Eversull | ................. A61M 25/10 604/103.01 |
| 7,713,281 B2* | 5/2010 | Leeflang | ............ A61B 17/3439 606/194 |

* cited by examiner

*Primary Examiner* — Manuel Mendez
(74) *Attorney, Agent, or Firm* — Dicke, Billig & Czaja, PLLC (57) ABSTRACT

The various embodiments disclosed herein relate to introducer sheaths having an expandable and retractable shaft configured to receive a positionable medical device therethrough. In some embodiments, the shaft is selectively expandable and retractable based on the position of the positionable device within the shaft.

18 Claims, 9 Drawing Sheets

EXPANDABLE INTRODUCER SHEATH AND RELATED METHODS

CROSS-REFERENCE TO RELATED APPLICATION

This application claims the benefit under 35 U.S.C. §119 (e) to U.S. Provisional Application 61/915,108, filed Dec. 12, 2013 and entitled "Expandable Introducer Sheath and Related Methods," which is hereby incorporated herein by reference in its entirety.

FIELD OF THE INVENTION

The various embodiments disclosed herein relate to introducer sheaths for introduction of other devices to an internal tissue, organ, or cavity of a patient. Various sheath embodiments have expandable and retractable tubular shafts that allow for selective expansion of the shafts as devices are passed through, thereby reducing damage to surrounding tissues by reducing contact with those tissues and eliminate the need to exchange sheaths of different sizes.

BACKGROUND OF THE INVENTION

Access for medical procedures has always been an important aspect for minimally invasive percutaneous interventional procedures, including endovascular procedures that require access to the venous or arterial system, or procedures that simply require access to an interior body cavity. In general, it is desirable to make the smallest incision point with the shortest tissue contact time when entering the body. Small incisions and short tissue contact time generally lead to improved patient outcomes, less complications, and less trauma to the vessels or organs being accessed, as well as to the skin and tissue through which the access point is created.

Innovations in percutaneous procedures continue and new devices and device concepts are introduced continually. In recent years, there has for example been high interest in placing structural elements (such as heart valves, heart valve repair devices, occluders (PFO, ASD, appendage, etc), grafts, electrical stimulators, leads, etc) percutaneously. One issue that physicians face is that these are often very large devices that require very large sheaths to deliver them to the intended site within the body. Sheath sizes of 16-24 F (0.21"-0.315") are commonly used for these procedures. As a result, access site trauma has been increasing; often resulting in vessel damage, excessive bleeding, increased case time, increased risk of infection, and increased hospitalization time.

To reduce access trauma, physicians try to use the smallest devices possible and place the smallest sheath size. This can be problematic, however, if during the procedure they discover a larger device is needed. This leads to a need to upsize the sheath, which is a lengthy procedure and leads to increased risk to the patient. Companies have tried to respond to these challenges by designing the smallest devices possible.

Some companies, such as Edwards Lifesciences and Terumo, have offered expandable sheaths that can be expanded within the body and thus do not require removal to upsize. The Edwards device is a slit sheath that overlaps radially and the Terumo device expands by inflating a balloon in the sheath. Both of these designs still have considerable problems.

A slit sheath design is problematic because increasing the perimeter of the sheath by moving the overlapping section still does not increase the diameter of the sheath significantly. This is due to the ratio of perimeter to area in a circle. Increasing the perimeter of a circle increases the area by a much smaller amount. Thus these known devices only increase in size by approximately 2 F (0.026" diameter). Also, such a design contains sharp edges that can damage a vessel.

The balloon expandable design expands to a greater degree than the slit design, but has other drawbacks including added steps and complexity to use, minimal control over expansion, potential trauma due to the large expansion force when the balloon is inflated, and the inability to recoil during use, thus resulting in continual compression of tissue during a procedure.

Both slit sheath and balloon expandable designs also have a major drawback in that they are not 'regionally' expansive along the length of the sheath, but instead the entire length of the sheath needs to be expanded or not expanded. Further, these sheaths are not very recoverable when not passing a large device through them—thus not 'retractable' to the original small size. These issues contribute to vascular trauma.

There is a need in the art for an improved introducer sheath and related methods.

BRIEF SUMMARY OF THE INVENTION

Discussed herein are various introducer sheaths, each having an expandable and recoverable tubular shaft that is configured to receive a positionable medical device.

In Example 1, an introducer sheath comprises an expandable and recoverable tubular shaft and a proximal hub operably coupled to a proximal end of the tubular shaft. The tubular shaft has a lumen sized and expandable to receive a positionable medical device therethrough.

Example 2 relates to the sheath according to Example 1, wherein the expandable and recoverable shaft is configured to expand solely at a location where the positionable medical device is positioned within the shaft.

Example 3 relates to the sheath according to Example 1, wherein the expandable and recoverable shaft is configured to expand along its entire length when the positionable medical device is positioned within the shaft.

Example 4 relates to the sheath according to Example 1, wherein the expandable and recoverable shaft is further configured to be retractable to an unexpanded state when the positionable medical device is removed.

Example 5 relates to the sheath according to Example 4, wherein the expandable and recoverable shaft is further configured to be self-retractable to an unexpanded state when the positionable medical device is removed.

Example 6 relates to the sheath according to Example 1, wherein the expandable and recoverable shaft is mechanically expandable or self-expandable.

Example 7 relates to the sheath according to Example 1, wherein the expandable and recoverable shaft is slit-less.

Example 8 relates to the sheath according to Example 1, wherein the expandable and recoverable shaft comprises an expandable mesh layer.

Example 9 relates to the sheath according to Example 1, wherein the expandable and recoverable shaft comprises at least two expandable mesh layers.

Example 10 relates to the sheath according to Example 1, wherein the tubular shaft further comprises a sealing layer disposed along a proximal length of the shaft.

Example 11 relates to the sheath according to Example 1, wherein the tubular shaft further comprises a holding layer disposed along a length of the shaft.

In Example 12, an introducer sheath comprises a tubular shaft comprising an expandable and recoverable mesh layer, a sealing layer disposed along a proximal length of the shaft, and a proximal hub operably coupled to a proximal end of the tubular shaft. The shaft has a lumen sized and expandable to receive a positionable medical device therethrough, an unexpanded state, and an expanded state. The expandable and recoverable shaft is configured to expand to the expanded state solely at a location where the positionable medical device is positioned within the shaft and is further configured to retract to the unexpanded state when the positionable medical device is removed from the location.

Example 13 relates to the sheath according to Example 12, wherein the proximal hub comprises a luer lock.

Example 14 relates to the sheath according to Example 12, wherein the tubular shaft comprises at least two expandable and recoverable mesh layers.

Example 15 relates to the sheath according to Example 12, wherein the tubular shaft further comprises a holding layer disposed along a length of the shaft.

Example 16 relates to the sheath according to Example 12, further comprising at least one band disposed around the tubular shaft.

Example 17 relates to the sheath according to Example 12, further comprising a longitudinal member disposed along a length of the shaft, wherein the longitudinal member comprises a longitudinal actuating member or a longitudinal structural member.

In Example 18, an introducer sheath comprises an expandable and retractable tubular shaft comprising an expandable and retractable mesh layer, a sealing layer disposed along a proximal length of the shaft, a holding layer disposed along a length of the shaft; and a proximal hub operably coupled to a proximal end of the tubular shaft. The tubular shaft has a lumen sized and expandable to receive a positionable medical device therethrough. The expandable shaft is configured to expand solely at a location where the positionable medical device is positioned within the shaft and is further configured to retract to an unexpanded state when the positionable medical device is removed from the location.

Example 19 relates to the sheath according to Example 18, wherein the expandable and retractable shaft comprises at least two expandable and retractable mesh layers.

Example 20 relates to the sheath according to Example 18, wherein the expandable and retractable mesh layer is mechanically expandable, self-expandable, mechanically retractable, or self-retractable.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed herein relate to an introducer sheath that has a selectively expandable diameter to allow the passage of a large device therethrough and further is configured to return to its original diameter upon passage of the device. In certain embodiments, the sheath is expandable to a much larger diameter than known introducer sheaths. Other implementations are configured to allow expansion only in the region of the sheath through which the device being passed through the sheath is positioned. Further embodiments have a sheath configured to allow recovery to its original diameter or even a smaller diameter after the device has been removed. The various embodiments can reduce damage to surrounding tissues by reducing contact with those tissues and eliminate the need to exchange sheaths of different sizes. As a result, in comparison to known sheaths, these embodiments can reduce procedure time, vascular trauma, bleeding, and the resulting risk of infection and other complications.

Figure 1A:
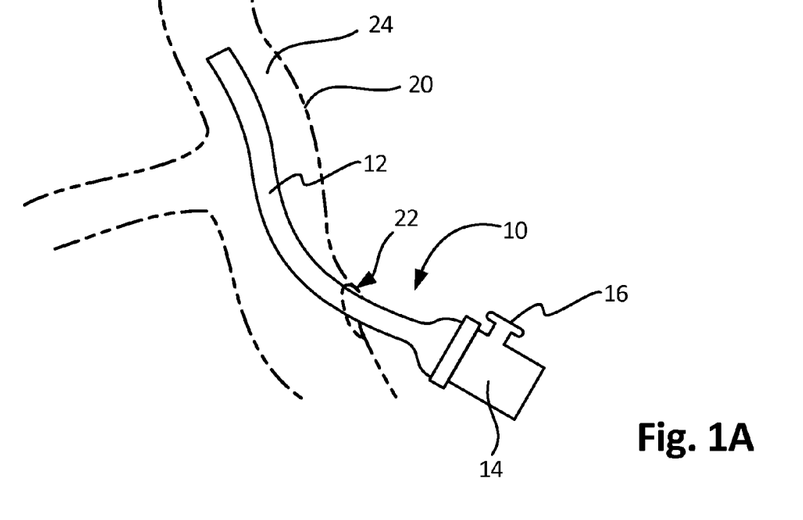
FIG. 1A is a cutaway view of an introducer sheath that has been positioned into a vessel of a patient, according to one embodiment.
Figure 1B:
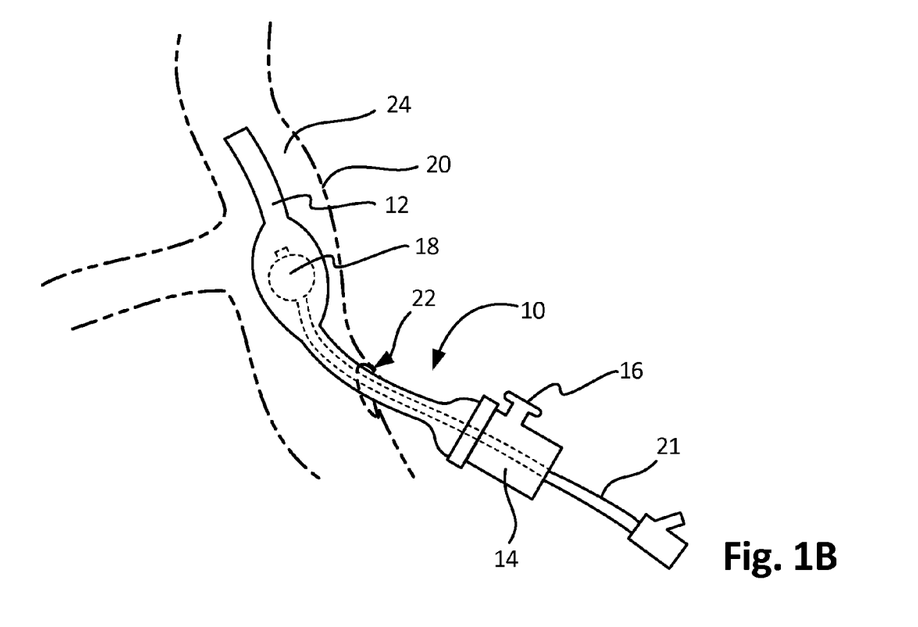
FIG. 1B is a cutaway view of the introducer sheath of FIG. 1A with another device 21 being advanced through the sheath.

FIGS. 1A and 1B depict one embodiment of an introducer sheath 10 that has been positioned through an incision 22 in the skin 20 and into a vessel 24 of a patient. The sheath 10 has a tubular shaft 12, a proximal hub 14 with a hemostatic seal, and a luer lock 16. Alternatively, the proximal hub 14 can have an extension line. FIG. 1A shows the sheath 10 positioned in the vessel 24 in its normal, "unexpanded" state, while FIG. 1B shows the sheath 10 with another device 21 being advanced through the sheath 10 such that the tubular shaft 12 expands or deforms at the location where the device 21 is passing through, which is depicted as the expanded region 18 of the shaft 12, and then retracts or recovers to its original diameter after the device 21 moves past or is removed from that region 18.

Thus, in various implementations, the tubular shaft 12 is configured to be expandable and retractable. In certain embodiments, the expandability of the shaft 12 (and any shaft described according to any embodiment set forth herein) is achieved via the elasticity of the shaft 12, which can result in the shaft 12 being either "self-expandable" (or "self-expanding") or "mechanically expandable" (or "mechanically expanding"). For purposes of this application, self-expandable means that the shaft 12 is configured to expand to a predetermined or nominal diameter automatically (without any type of actuation, mechanical or otherwise). Further, for purposes of this application, mechanically expandable means that the shaft 12 is configured to expand when a positionable medical device as defined below is positioned through the shaft 12. That is, the device itself that is being passed through the shaft 12 causes the expansion of the shaft 12. Alternatively, the expandable characteristics of the shaft 12 can be caused by something other than elasticity.

After passage of the device, the shaft 12 is configured to be contractable, retractable, or recoverable to its original, unexpanded state as depicted in FIG. 1A. The retractability can be, in certain embodiments, achieved by the elasticity of the shaft 12, which can result in the shaft 12 being either "self-retractable" (or "self-retracting," "self-recoverable," or "self-contractable") or "mechanically retractable" (or "mechanically retracting," "mechanically recoverable," or "mechanically contractable"). For purposes of this application, self-retractable means that the shaft 12 is configured to retract to a predetermined or nominal diameter automatically (without any type of actuation, mechanical or otherwise). Further, for purposes of this application, mechanically retractable means that the shaft 12 is configured to retract when a device or component is used to cause the shaft 12 to retract or recover. Alternatively, the retractable characteristics of the shaft 12 can be caused by something other than elasticity.

For purposes of this application, any device that can be positioned through an introducer sheath according to any embodiment disclosed or contemplated herein can be referred to as a "positionable medical device" or "insertable medical device." Such devices include guidewires, dilators, delivery devices (for delivery and/or placement of structural elements such as heart valves, heart valve repair devices, occluders, grafts, electrical stimulators, leads, etc.), guide catheters, guiding sheaths, diagnostic catheters, stent delivery systems, balloon catheters, and other known vascular devices. Other devices can include non-vascular devices such as scopes and other common surgical instruments. Further, the introducer sheath is configured to receive tissues or organs.

Figure 1C:
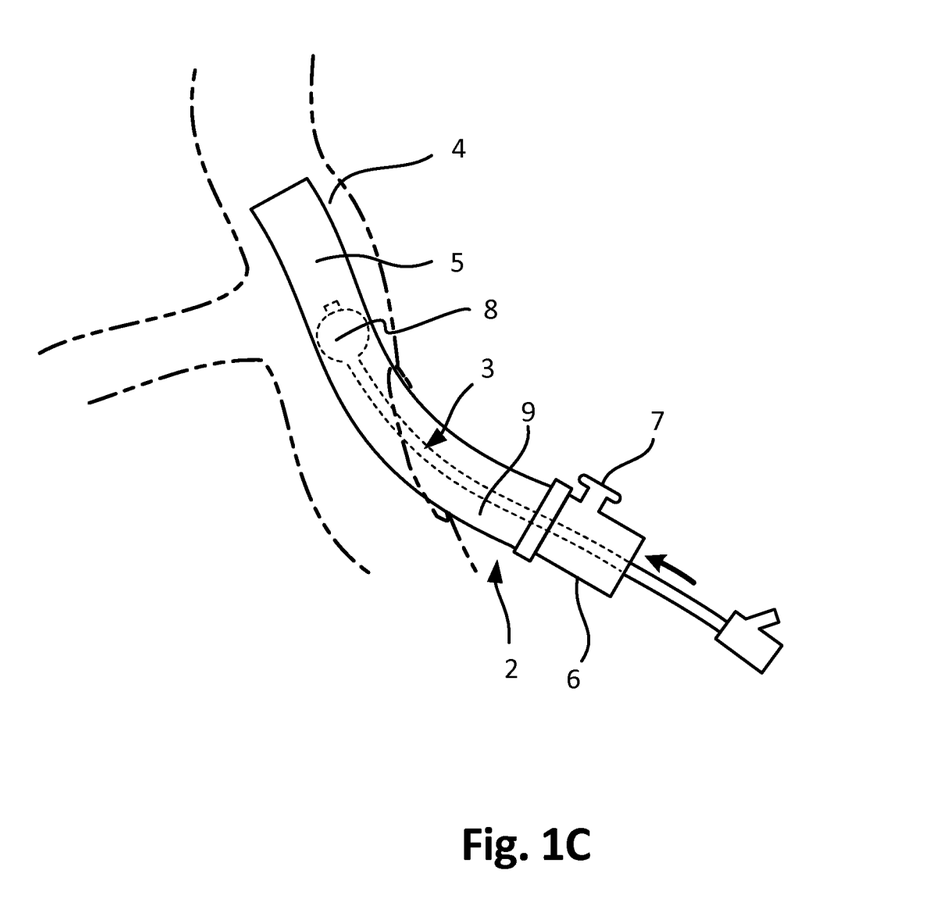
FIG. 1C is a cutaway view of an introducer sheath that has been positioned into a vessel of a patient, according to another embodiment.

FIG. 1C depicts another embodiment of an introducer sheath 2 that has been positioned through an incision 3 and into a vessel 4 of a patient. In this implementation, the sheath 2 is configured to expand along its entire length from its normal unexpanded state when a device is positioned through the sheath such that the entire sheath 2 is in an expanded state. The sheath 2 has a tubular shaft 5, a proximal hub 6 with a hemostatic seal, and a luer lock 7. The sheath 2 can have a normal, "unexpanded" state similar to the unexpanded state of the embodiment depicted in FIG. 1A, while FIG. 1C shows the sheath 2 with another device 8 being advanced through the sheath 2 such that the sheath 2 expands or deforms along its full length when device 8 is passing through, which is depicted as the expanded region 9 of the shaft 5. After passage of the device 8, sheath 2 contracts to its original, unexpanded state similar to that depicted in FIG. 1A.

While the sheath 10 discussed above and depicted in FIGS. 1A and 1B and its components will be further referenced below in the description of various embodiments, it is understood that these descriptions apply equally to the sheath 2 in FIG. 1C and any other embodiments contemplated herein.

The shaft 12 has one or more layers. In certain embodiments, the shaft 12 has an expandable layer such as the expandable layer 28 shown in FIG. 2. In other embodiments, the shaft 12 can have both an expandable layer and a holding layer, such as the holding layer 102 depicted in FIG. 6 and discussed below.

Figure 2:
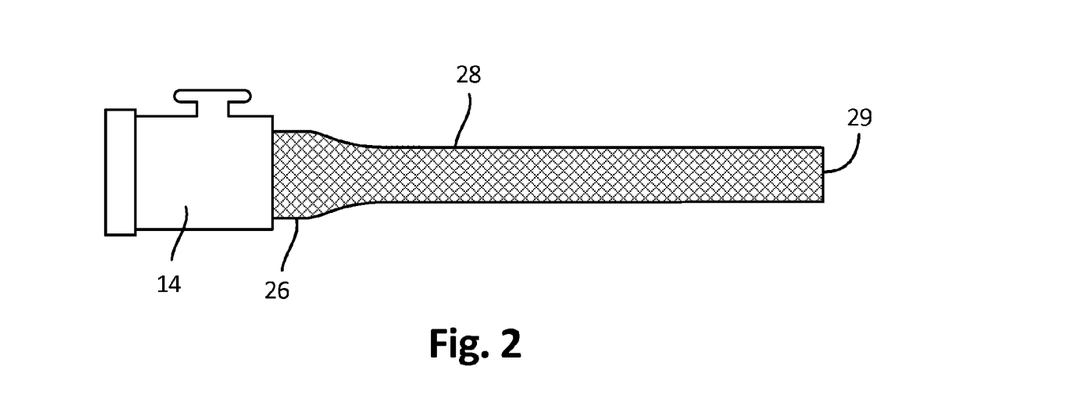
FIG. 2 is a side view of an introducer sheath with a shaft having an expandable layer, according to one embodiment.

FIG. 2 depicts a shaft 12 having an expandable layer 28, according to one implementation. The expandable layer 28 is a mesh layer 28 that can consist of a series of intertwined members that form a matrix, such as a braided configuration, coiled configuration, a laser cut configuration, a woven configuration, a nylon stocking-like configuration, or the like. Alternatively, the mesh layer 28 can be a lattice structure having deformable struts. If the mesh layer 28 has a braided configuration, the braid can be a single wire woven braid, or multiple wires. The mesh layer 28, according to certain embodiments, has multiple individual overlapping components (wires) that create a defined structure, yet because they are not rigidly affixed to one another, they allow for movement of the components in relation to each other and expansion, characteristics that are useful in the embodiments described herein. It is understood that any expandable layer component described in any of the embodiments disclosed or contemplated herein can have any of the characteristics described above or elsewhere with respect to expandable layers or mesh layers.

In one implementation, the mesh layer 28 is made of fine metal wire, such as stainless steel or nitinol. Alternatively, the mesh layer 28 can be polymeric.

Each of the various shaft embodiments disclosed or contemplated herein (including, for example, shaft 12 described above or any other shaft described below) can be a shaft that has no slits (also referred to as "slitless"). For example, certain expandable mesh layer 28 embodiments have no slits. Alternatively, the expandable layer 28 can be a unitary component such as a tubular component with deformable strut-like structures that are separated by pores or slits formed in the layer to create a scaffold or helical configuration, resulting in an expandable layer 28. The scaffold or helical configuration can be formed by a laser, molding, or other such means. In a further alternative, the expandable layer 28 is made of an elastic material that is expandable or deformable.

In accordance with one embodiment, the pores or openings in the expandable layer 28 range in diameter from about 1 to about 1500 microns. Alternatively, the pores have a diameter that is equal to or less than about 1000 microns. In a further alternative, the pores have a diameter that is equal to or less than 500 microns.

According to certain embodiments, such as the sheath 10 in FIGS. 1A and 1B, the expandable layer 28 is configured such that the diameter only expands at the location where the specific local force is applied to it. That is, the expandable layer 28 with a device or other object 18 being advanced through the expandable layer 28 takes on shape similar to that of a snake that has eaten a large mouse and only deforms or expands where necessary. This feature of the expandable layer 28 can reduce the amount of contact forces and the amount of contact time with the internal surfaces of the patient during a procedure (such as the inner wall of the vessel 24 in which the shaft 12 is positioned in FIG. 1B). In these embodiments, the expandable layer 28 is configured to expand solely at the location of the object 18 and then easily return (or "recover") to its normal, unexpanded state. As a result, upon delivery or appropriate positioning of the device that was advanced through the expandable layer 28, the expandable layer 28 returns to a diameter that is substantially the same as its unexpanded diameter, thereby making the removal of the expandable layer 28 from the vessel (such as vessel 24 discussed above) easier.

In certain alternative embodiments, such as the sheath 2 shown in FIG. 1C, the expandable layer (similar to expandable layer 28) is configured such that the entire sheath diameter expands when the specific local force is applied to a portion of it. That is, a device or other object 8 being advanced through the shaft 5 causes the entire sheath 2 to expand. In these embodiments, the shaft 5 (including any layers therein, such as an expandable layer) is configured to easily return (or "recover") to its normal, unexpanded state once the device 8 has passed and the local force is no longer being applied. This feature of the shaft 5 can reduce the amount of contact forces and the amount of contact time with the internal surfaces of the patient during a procedure (such as the inner wall of the vessel 4 in which the shaft 5 is positioned in FIG. 1C). In these embodiments, the shaft 5 is configured to easily return (or "recover") to its normal, unexpanded state.

In accordance with one embodiment, the expandable layer 28 is configured to recoil or return to an unexpanded diameter that is substantially the same unexpanded diameter as the expandable layer 28 had prior to expansion. Alternatively, the layer 28 returns to an unexpanded diameter that is within 1 mm of its original unexpanded diameter. In one implementation, the return force is equal to or less than about 0.3 lb. According to certain embodiments, this ability to return to the unexpanded state is possible because the layer 28 is made of a shape-memory material.

It is understood that, in accordance with certain implementations, all the layers of the shaft 12 are configured to deform or expand only where necessary. That is, the expansion and retraction characteristics of the expandable layer 28 cause the entire shaft 12 to have similar characteristics.

The shaft 12, according to one embodiment, has a diameter ranging from about 5 French to about 28 French. In one exemplary implementation, the shaft 12 has a diameter of from about 12 French to about 24 French, while another exemplary implementation has a diameter of from about 12 French to about 18 French, and a further exemplary implementation has a diameter of from about 18 French to about 24 French. According to another exemplary implementation, the shaft 12 has a diameter of from about 5 French to about 12 French, while another embodiment has a diameter of from about 5 to about 8 French, and a further embodiment has a diameter of from about 8 to about 12 French.

In certain embodiments, the shaft 12 is configured to expand from an unexpanded diameter to an expanded diameter that is at least 10 French larger than the unexpanded diameter. Alternatively, the shaft 12 is configured to expand to an expanded diameter that is at least 8 French larger than the unexpanded diameter. In a further alternative, the shaft 12 can expand to an expanded diameter that is at least 6 French larger than the unexpanded diameter. In yet another alternative, the shaft 12 is configured to expand to an expanded diameter that is at least 4 French larger than the unexpanded diameter. Alternatively, the shaft 12 is configured to have an expanded diameter that is at least 3 French larger. For example, one shaft 12 embodiment can expand from an unexpanded diameter of 14 French to an expanded diameter of 22 French, while another embodiment can expand from an unexpanded diameter of 18 French to an expanded diameter of 26 French. In certain of the embodiments described herein, the expansion is possible because the expandable layer is made of a shape memory material.

In one implementation, the change in diameter of the shaft 12 causes the length of the shaft 12 to vary by about 20 mm or less. Alternatively, the variation in the length of the shaft 12 is about 10 mm or less. In a further alternative, the length of the shaft 12 varies by about 1 mm or less.

According to one embodiment, the shaft 12 can have a length that ranges from about 3 cm to about 100 cm. Alternatively, the shaft 12 ranges from about 5 cm to about 50 cm. In a further alternative, the shaft 12 ranges from about 10 to about 25 cm. In yet another alternative, the shaft 12 has a length of about 15 cm.

In accordance with one implementation, the wall of the shaft 12 has a thickness ranging from about 0.01 to about 0.10 inches. Alternatively, the wall has a thickness of from about 0.02 to about 0.08 inches. In a further embodiment, the wall has a thickness of equal to or less than about 0.075 inches.

According to certain embodiments, the expandable layer 28 has a collapse resistance. For purposes of this application, "collapse resistance" is the hoop strength of the expandable layer 28 and is also referred to as "radial force." In one embodiment, the collapse resistance ranges from about 0.05 lb. to about 1.0 lb. Alternatively, the collapse resistance is from about 0.25 to about 0.75 lb. In a further embodiment, the collapse resistance is at least about 0.5 lb.

Returning to the expandable layer 28, in accordance with one implementation, the layer 28 can be fully or partially coated with an elastic, impermeable coating. For example, the coating can be made of PTFE, silicone, urethane, low durometer PEBAX, latex, spray silicone, hydrophilics, or the like. Alternatively, the coating can be any known coating for use in implantable medical devices.

In certain embodiments, the expandable layer 28 is a single layer. For example, as best shown in FIG. 2, the layer 28 of sheath 10 is a single mesh layer 28. Further, the layer 28 has a large section 26 at a proximal end of the layer 28 where it is coupled to the proximal hub 14. The large section 26 has a larger diameter than the rest of the layer 28, thereby allowing the layer 28 to be successfully coupled to the hub 14 at the proximal end of the layer 28.

Figure 3:
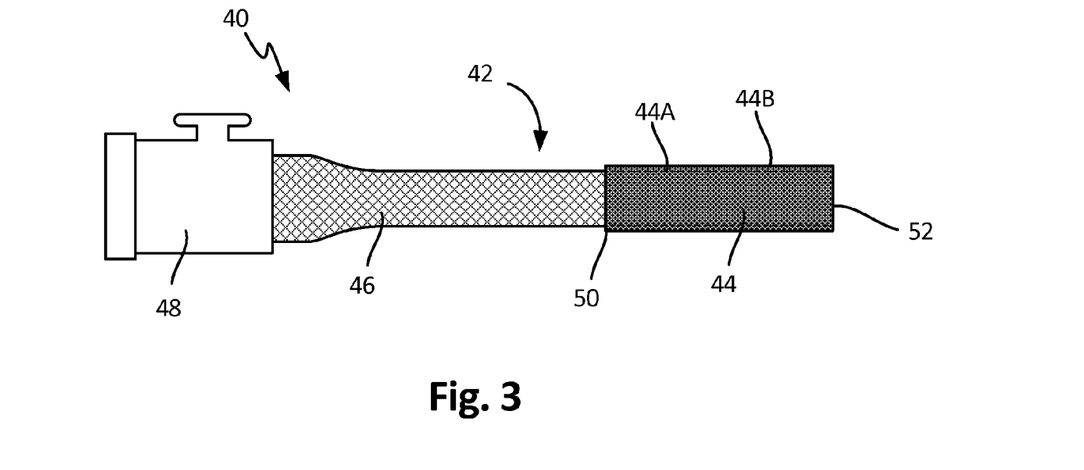
FIG. 3 is a side view of an introducer sheath with a shaft having two expandable layers, according to one embodiment.

Alternatively, the expandable layer can be two layers along at least a portion of the length of the shaft 12. For example, FIG. 3 depicts a sheath 40 having a shaft 42 that has a distal portion with two expandable layers 44 that, in this embodiment, are mesh layers 44 (also referred to as a "dual mesh layer") and a proximal portion with a single expandable layer 46 (which, in this embodiment, is a mesh layer 46). The dual mesh layer 44 is made up of an inner layer 44A and an outer layer 44B. According to one embodiment, the dual expandable layer 44 can make up at least 5% of the total length of the shaft 42. Alternatively, the dual expandable layer 44 can make up anywhere from about 1% to about 100% of the total length of the shaft 42. In those implementations in which the dual expandable layer 44 makes up 100% of the shaft 42, both layers 44A, 44B can be coupled to the proximal hub 48. In a further alternative, the shaft 40 can have a multiple expandable layer that has three or more layers.

According to one implementation, the dual expandable layer 44 (or a multiple expandable layer (not shown) can be formed by folding a single expandable layer back over on itself. For example, in FIG. 2, the distal end 50 of the expandable layer 44 was folded back over itself externally to create the outer layer 44B over the inner layer 44A. Alternatively, the expandable layer can be folded back internally. The folding or rolling method eliminates any sharp edges or stray strands or wires protruding from an edge at the unfolded distal end 50 of the layer by folding or rolling that distal end back, thereby creating a "new" distal end 52 of the shaft 42 that does not have any sharp edges or stray strands or wires. Alternatively, instead of a fold, the end of the shaft can have a "finished" end in which there are no sharp edges or stray strands or wires. For example, according to one embodiment, the mesh layer 28 in FIG. 2 can be a single woven braid configured such that the distal end 29 has no sharp wires extending therefrom and instead has a "smooth" or "finished" end 29.

Figure 4:
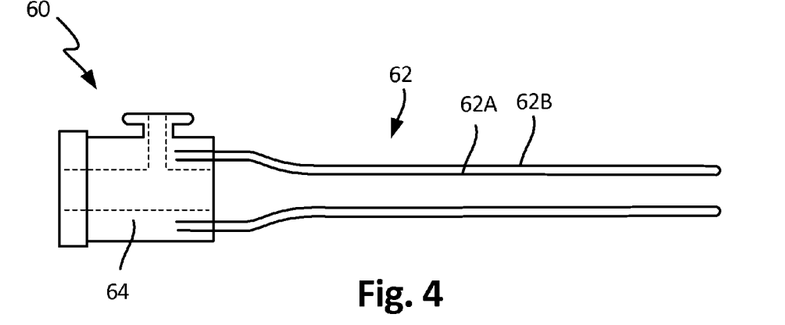
FIG. 4 is a side view of another introducer sheath with a shaft having two expandable layers, according to another embodiment.

As another example of a shaft with an expandable layer that is folded over, FIG. 4 depicts a sheath embodiment 60 in which the shaft 62 has an expandable mesh layer 62 that is folded over such that the dual layer 62A, 62B extends along 100% of the length of the shaft 62. In this implementation, the ends of both the inner layer 62A and the outer layer 62B are coupled to the proximal hub 64.

Figure 5A:
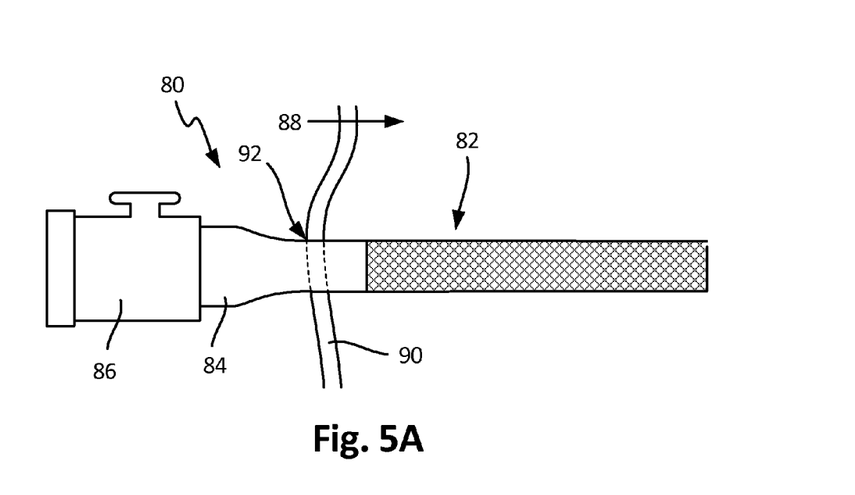
FIG. 5A is a side view of an introducer sheath with a sealing layer, according to one embodiment.

FIG. 5A shows a sheath 80 with a sealing layer 84 (also referred to herein as a "hemostatic layer") positioned along a portion of the shaft 82, according to one implementation. In this embodiment, the sealing layer 84 is positioned along a proximal portion of the shaft 82 such that the layer 84 is coupled to or in contact with the proximal hub 86. The sealing layer 84 is non-porous, substantially non-porous, or has reduced porosity in comparison to the shaft 82. The layer 84 can be elastomeric and have sealing characteristics (such as, for example, silicone or latex). Alternatively, the layer 84 can be a substantially rigid material and have slits or other geometry or features that allow for some expansion of the layer 84.

As shown in FIG. 5A, the sheath 80 is depicted as being positioned through an incision 92 in the wall 90 of a vessel 88 of a patient. The sealing layer 84 is configured to provide reduced porosity that helps to prevent fluid from migrating through the layers of the sheath 82 in the region of the sealing layer 84. This reduced porosity creates a fluidic seal when the sheath 82 is placed through a vessel wall such as the wall 90 as shown in FIG. 5A.

Figure 5B:
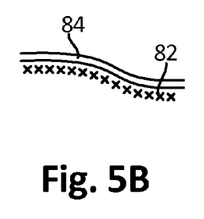
FIG. 5B is a cross-sectional view of a sealing layer, according to one embodiment.
Figure 5C:
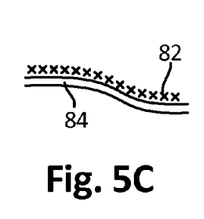
FIG. 5C is a cross-sectional view of another sealing layer, according to another embodiment.
Figure 5D:
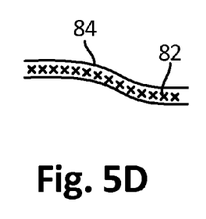
FIG. 5D is a cross-sectional view of another sealing layer, according to a further embodiment.
Figure 5E:
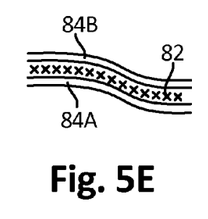
FIG. 5E is a cross-sectional view of a further sealing layer, according to yet another embodiment.

As shown in FIGS. 5B-5E, the sealing layer 84 can be positioned along the shaft 82 according to various configurations. That is, as shown in FIG. 5B, the sealing layer 84 can be positioned externally in relation to the shaft 82. Alternatively, as shown in FIG. 5C, the layer 84 can be positioned internally in relation to the shaft 82. In another alternative, as shown in FIG. 5D, the sealing layer 84 is embedded within the shaft 82 (or vice versa) such that the layer 84 and shaft 82 constitute a single, integral layer 82, 84. In yet a further alternative, as shown in FIG. 5E, two sealing layers 84 are positioned on either side of the shaft 82 such that there is both an internal sealing layer 84A and an external sealing layer 84B. It is understood that the shaft 82 constitutes at least an expandable layer (like the expandable layer 28 discussed above).

Figure 6:
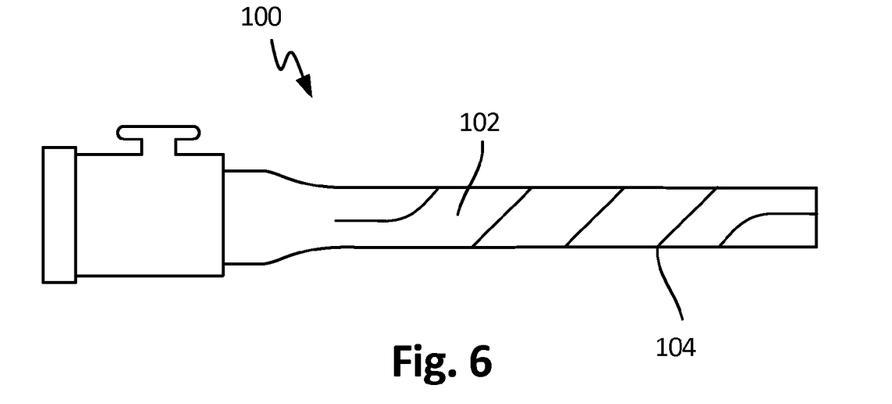
FIG. 6 is a side view of an introducer sheath having a holding layer, according to one embodiment.

As mentioned above, in accordance with certain embodiments, the shaft of any introducer sheath embodiment disclose or contemplated herein can also optionally have at least one holding layer, which can be made of continuous or unitary material which defines the inner and/or outer diameter of the shaft. For example, FIG. 6 shows one implementation of an introducer sheath 100 having a holding layer 102. The holding layer 102 is configured to be positioned alongside the expandable layer (not shown) but allows the individual members of the expandable layer (such as wires of a mesh layer) to move or slide independently of the holding layer 102. In one embodiment, the holding layer 102 is elastomeric. Alternatively, the layer 102 is semi-rigid or substantially rigid. In those embodiments in which the layer 102 is at least semi-rigid, such as the embodiment shown in FIG. 6, the layer 102 can have a spiral slit pattern 104 formed in the layer 102 to allow the layer 102 to expand.

In certain embodiments, the holding layer 102 can be configured to mechanically restrict the expandable layer from expanding to its natural or nominal state of expansion.

The holding layer 102 or any other holding layer embodiment disclosed or contemplated herein can be made of a continuous or unitary material such as PTFE or HDPE. The material can be lubricious or alternatively can be coated with a lubricious coating.

Figure 7:
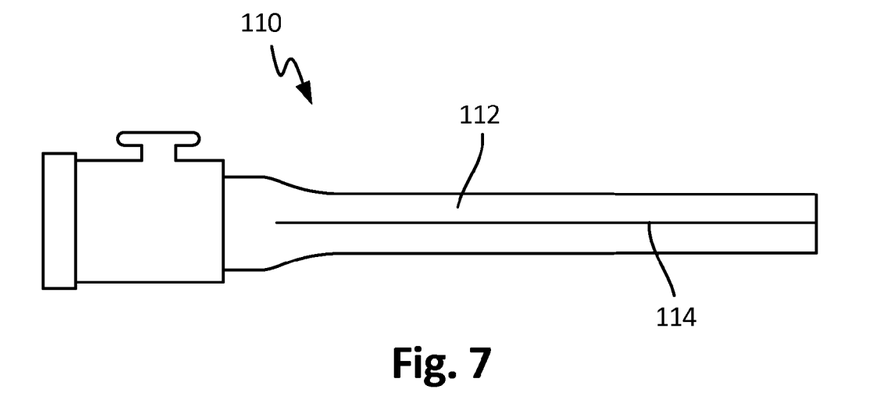
FIG. 7 is a side view of another introducer sheath having a holding layer, according to another embodiment.

FIG. 7 shows another implementation of a sheath 110 having a holding layer 112. In this embodiment, the layer 112 has a straight slit pattern 114 formed in the layer 112 to allow expansion. Alternatively, the slit pattern can be spiral, or any shape or configuration that allows for the holding layer 112 to increase diameter. The layer 112 can also be made to be porous with strut-like members that deform to increase the overall diameter. Alternatively, the layer 112 could be fluted so that expanding the flutes leads to a larger diameter of the layer 112.

Figure 8A:
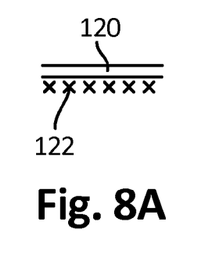
FIG. 8A is a cross-sectional view of a holding layer, according to one embodiment.
Figure 8B:
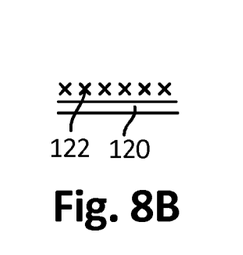
FIG. 8B is a cross-sectional view of another holding layer, according to another embodiment.
Figure 8C:
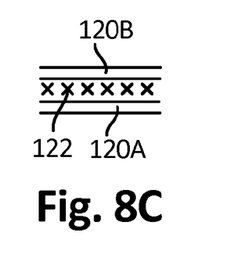
FIG. 8C is a cross-sectional view of yet another holding layer, according to a further embodiment.

As shown in FIGS. 8A-8C, a holding layer 120 can be positioned along the shaft according to various configurations. That is, as shown in FIG. 8A, the holding layer 120 can be positioned externally in relation to the expandable layer 122. Alternatively, as shown in FIG. 8B, the layer 120 can be positioned internally in relation to the expandable layer 122. In another alternative, two holding layers 120A, 120B are positioned on either side of the expandable layer 122 such that there is both an internal holding layer 120A and an external holding layer 120B. In a further alternative, the layer 120 is embedded within the expandable layer 122 (or vice versa), or the expandable layer 122 is encapsulated by the holding layer 120 such that the layer 120 and expandable layer 122 constitute a single, integral layer 120, 122 (not shown). It is also understood that various sheath embodiments do not have a holding layer.

According to certain implementations, the holding layer can also be the sealing layer described above with respect to FIGS. 5A-5E. Alternatively, the holding layer and sealing layer can be separate layers of the shaft. In those embodiments in which the holding layer has a slit pattern or other configurations in which it is not possible to provide a seal, the shaft has both a holding layer and a sealing layer.

Figure 9:
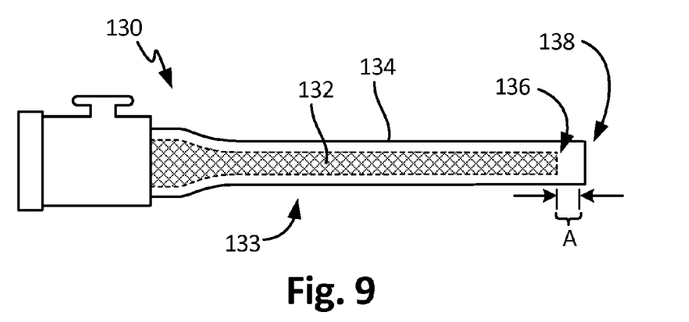
FIG. 9 is a side view of an introducer sheath having both a holding layer and an expandable layer, according to one embodiment.

FIG. 9 shows another implementation of a sheath 130 with a shaft 133 having both a holding layer 134 and an expandable layer 132. In this embodiment, the holding layer 134 is positioned externally in relation to the expandable layer 132. Further, this holding layer 134 embodiment is configured to have a distal end 138 that extends distally beyond the distal end 136 of the expandable layer 132 by an amount shown by the distance between the two lines, identified as A. In one embodiment, the distal end 138 of the holding layer 134 extends at least 1 mm beyond the distal end 136 of the expandable layer 132. Alternatively, the distal end 138 of the holding layer 134 can extend beyond the distal end 136 of the expandable layer 132 by an amount ranging from about 1 mm to about 3 cm.

Figure 10:
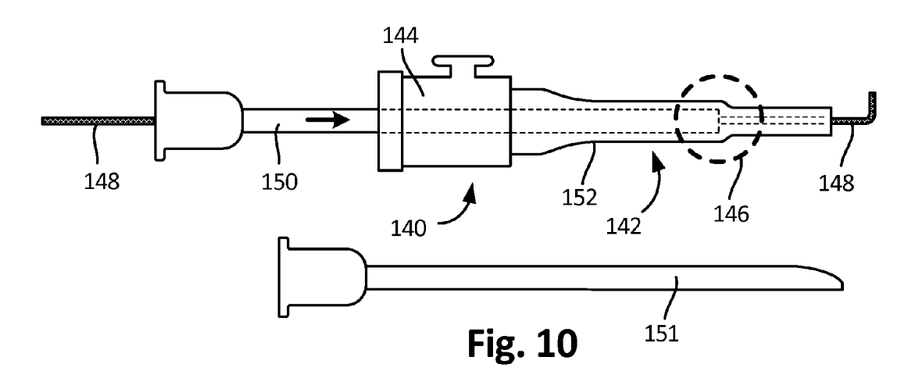
FIG. 10 is a side, cross-sectional view of an introducer sheath in combination with other tools used in conjunction with the sheath, according to one embodiment.

FIG. 10 depicts an introducer sheath 140, according to one embodiment, in combination with other devices/tools typically used in conjunction with such a sheath. The sheath 140 has a shaft 142 and a proximal hub 144. The shaft 142 in this embodiment is made up of a holding layer 152 and an expandable layer (not shown). In use, the sheath 140 is first positioned over a guidewire 148 and used in conjunction with a small dilator 151 (disposed into the sheath 140) to provide rigidity (also referred to as "column strength") to the assembly during the introduction of the assembly into the target vessel of the patient. This assembly is typically inserted into the patient's vessel before any other device or component. Subsequently, the small dilator 151 is removed from the sheath 140 and a larger dilator 150 is then inserted through the sheath 140 as shown to provide rigidity and expand the sheath 140 so that the tissue around the sheath 140 expands. More specifically, the encircled area identified as 146 depicts the distal end of the dilator 150 as it expands the shaft 142 of the sheath 140. According to alternative embodiments, the use of the guidewire 148 is optional.

Figure 11A:
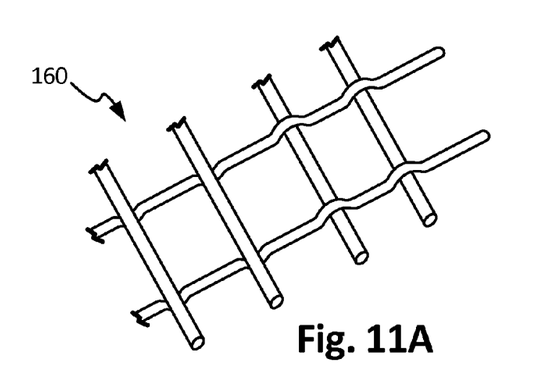
FIG. 11A is a perspective view of a braided mesh expandable layer of a shaft, according to one embodiment.
Figure 11B:
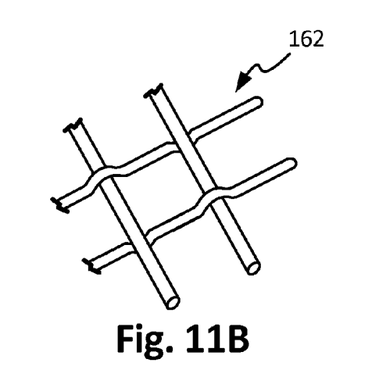
FIG. 11B is a perspective view of another braided mesh expandable layer of a shaft, according to another embodiment.

FIGS. 11A and 11B depict two versions of a shaft having a braided mesh expandable layer. More specifically, FIG. 11A shows a braided mesh layer 160 with a "two over, two under" pattern, while FIG. 11B shows a braided mesh layer 162 with a "one over, one under" pattern.

Figure 12:
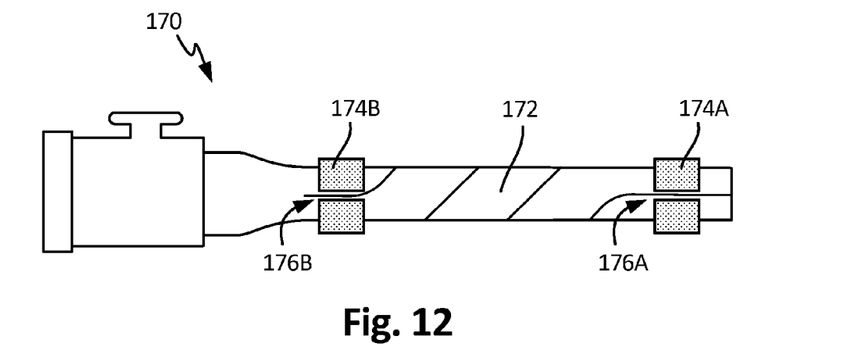
FIG. 12 is a side view of an introducer sheath having two bands positioned around the holding layer, according to one embodiment.

FIG. 12 shows an introducer sheath 170 with two bands 174A, 174B positioned around the holding layer 172. Alternatively, the bands 174A, 174B can be positioned around the expandable layer (not shown) when no holding layer is present. The bands 174A, 174B, in certain embodiments, can be integrated into either the holding layer 172 or the expandable layer and can either be positioned externally to the holding layer or expandable layer or alternatively can be positioned internally within the holding layer or expandable layer. The bands 174A, 174B are configured to apply a radial force to urge or compress the sheath 170 to return to its original diameter, such as its normal or unexpanded diameter. In a further embodiment, the bands 174A, 174B can also help constrain components such as the members in the expandable mesh (not shown) or at the edge of the expandable mesh (not shown). The bands 174A, 174B can be placed anywhere along the length of the sheath 170.

The bands 174A, 174B in this embodiment are substantially rigid and each has a slit 176A, 176B configured to allow for expansion. Alternatively, the bands 174A, 174B can be elastomeric and expandable without a slit. The bands 174A, 174B can also be made of a shape-memory material such as nickel titanium (Nitinol), spring steel, or a polymer. In other embodiments, the bands 174A, 174B are radiopaque bands 174A, 174B or markers. While there are two bands 174A, 174B in this embodiment, it is contemplated that the sheath 170 can have one band or three or more bands. Of course, other embodiments have no bands. As such, the number of bands can range from zero to as many as can be placed along the length of the sheath 170. In a further embodiment in which the one or more bands are positioned around the expandable layer (not shown), the one or more bands can be coupled to both the expandable layer (not shown) and the holding layer 172, thereby coupling the expandable layer and holding layer 172.

It is understood that any of the components on the sheath 170 or any other sheath embodiment disclosed or contemplated herein might be made from a radiopaque material for visualization under x-ray.

Figure 13:
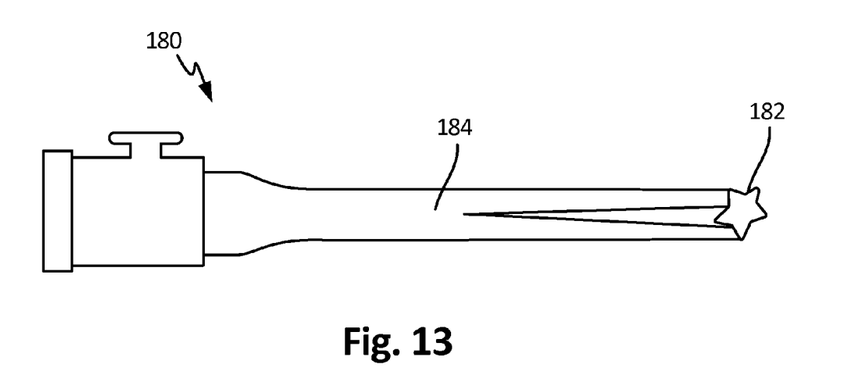
FIG. 13 is a side view of an introducer sheath having a holding layer with a fluted or scalloped design, according to one embodiment.

FIG. 13 depicts an introducer sheath 180 according to another embodiment, wherein the sheath 180 has a holding layer 184 with a fluted or scalloped design (non-round) 182 that can allow for expansion.

Figure 14:
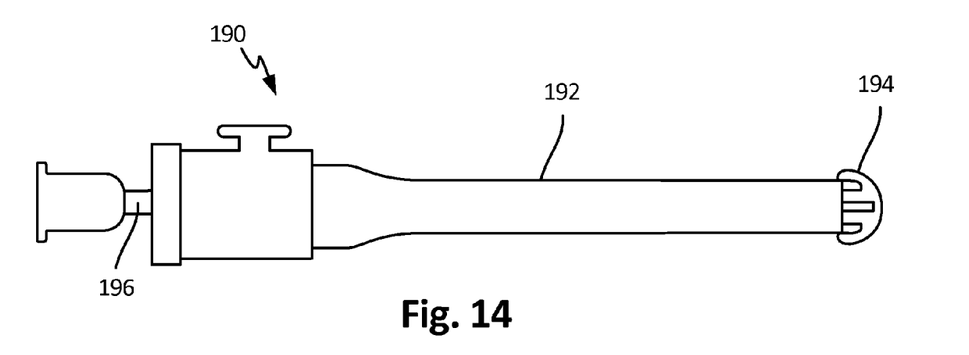
FIG. 14 is a side view of an introducer sheath having a nosecone coupled to the distal end of a dilator positioned therethrough, according to one embodiment.

FIG. 14 shows an introducer sheath 190 with a nosecone 194 coupled to the distal end of a dilator 196 such that the nosecone 194 can extend from the distal end of the shaft 192 to further cover the distal edges of the shaft 192 when the sheath 190 is being advanced and first being placed. The nosecone 194 can be retractable to form a smaller diameter. The nosecone 194 can be sized to just match the largest diameter of the shaft 192 to cover the leading edge or it can be larger in diameter and actually overlap a portion of it. The nosecone 194 can be a balloon or a material that is compressible or can be changed in shape to allow it to become smaller for removal.

Figure 15:
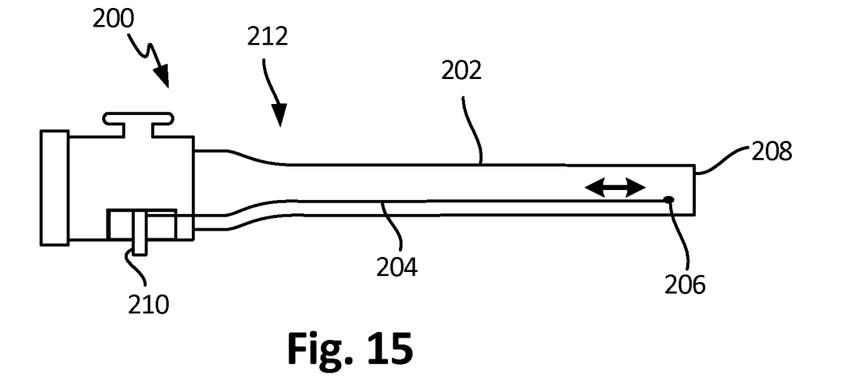
FIG. 15 is a side view of an introducer sheath having a longitudinal actuating member, according to one embodiment.

FIG. 15 depicts an introducer sheath 200 having a longitudinal actuating member 204 that is positioned in or near the expandable layer 202 of the shaft 212 and connected to an anchor point 206 at or near the distal end 208 of the expandable layer 202. The proximal end of the actuating member 204 has an actuating element such as sliding member 210 at its proximal end. In use, a user can actuate the sliding member 210 and thereby change the length of the expandable layer 202, in turn causing the expansion or reduction of the expandable layer 202 diameter. For example, a user could pull the sliding member 210 proximally, thereby urging the distal end 206 of the expandable layer 202 proximally and thus expanding the diameter of the expandable layer 202. Further, the user could also urge the sliding member 210 distally, thereby urging the distal end 206 distally and thus reduce the diameter of the expandable layer 202.

Figure 16:
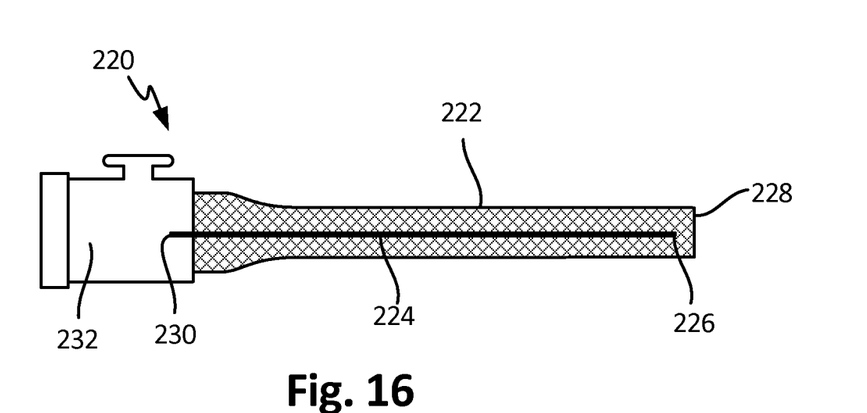
FIG. 16 is a side view of an introducer sheath having a longitudinal structural member, according to one embodiment.

Alternatively, FIG. 16 shows an introducer sheath 220 having a longitudinal structural member 224 that is positioned in or near the expandable layer 222 and connected to anchor point 226 at or near the distal end 228 and another anchor point 230 at or near the proximal end of the expandable layer 222 (or in the hub 232). The structural member 224 is substantially rigid and helps to restrain the expandable layer 222 from changing in length. The anchor points 226, 230 can be configured to uncouple from the structural member 224 if length change is desired—or may be designed so they are always coupled. Longitudinal structural member 224 may be separate from the expandable layer 222 or may be intertwined at one or more points within the expandable layer 222.

Figure 17:
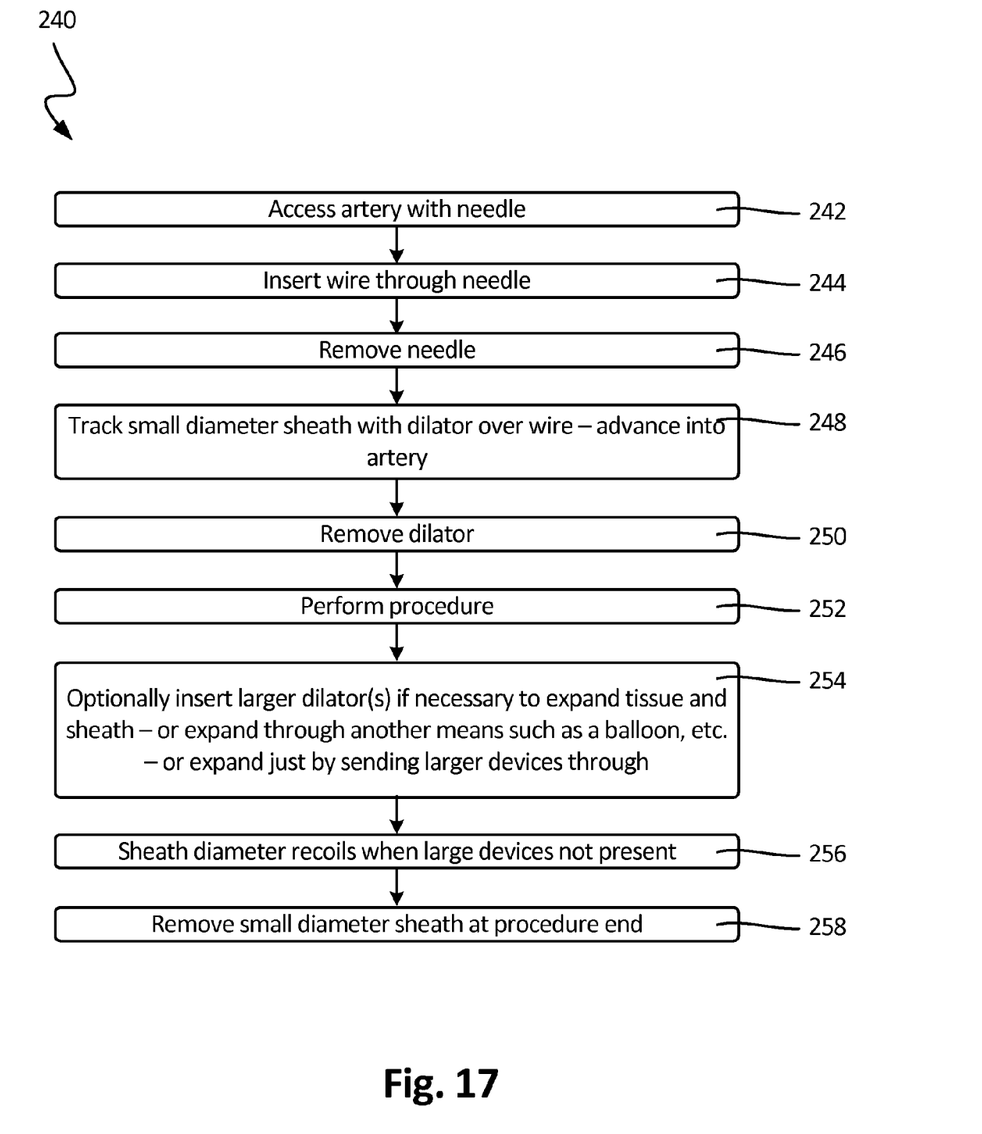
FIG. 17 is a flow chart relating to a method of using an introducer sheath, according to one embodiment.

In use, the introducer sheath embodiments disclosed herein provide greater flexibility for introduction of various devices into a patient's vessel in fewer steps and with reduced damage and complications. FIG. 17 sets forth a method of using an introducer sheath 240 as described herein, according to one embodiment. Prior to using the introducer sheath, a needle is used to access the target vessel (in this case, an artery) (block 242). A guidewire is then inserted through the needle (block 244), and the needle is removed (block 246). The introducer sheath (with a dilator positioned therein) is then urged distally over the guidewire and into the artery (block 248), and the dilator is then removed (block 250). Once the dilator is removed, the desired procedure can be performed through the introducer sheath. As bigger devices are required to be inserted through the sheath, the sheath can be expanded by either inserting a larger dilator (or dilators), a balloon, or simply by inserting the larger devices themselves (block 254). As described above, the shaft diameter returns to its unexpanded state when the large devices are passed through or removed (block 256). When the procedure is complete, the unneeded devices are removed through the sheath and then the sheath is removed (block 258).

Although the present invention has been described with reference to preferred embodiments, persons skilled in the art will recognize that changes may be made in form and detail without departing from the spirit and scope of the invention.

What is claimed is:

1. An introducer sheath comprising:
   (a) an expandable and recoverable tubular shaft comprising a lumen sized and expandable to receive a positionable medical device therethrough, wherein the expandable and recoverable tubular shaft includes an expandable mesh layer;
   (b) a sealing layer apart from the expandable and recoverable tubular shaft,
      wherein the sealing layer is positioned along the expandable and recoverable tubular shaft,
      and further wherein a porosity of the sealing layer is less than a porosity of the expandable and recoverable tubular shaft; and
   (c) a proximal hub operably coupled to a proximal end of the expandable and recoverable tubular shaft.

2. The sheath of claim 1, wherein the expandable and recoverable tubular shaft is configured to expand solely at a location where the positionable medical device is positioned within the expandable and recoverable tubular shaft.

3. The sheath of claim 1, wherein the expandable and recoverable tubular shaft is configured to expand along its entire length when the positionable medical device is positioned within the expandable and recoverable tubular shaft.

4. The sheath of claim 1, wherein the expandable and recoverable tubular shaft is further configured to be retractable to an unexpanded state when the positionable medical device is removed.

5. The sheath of claim 4, wherein the expandable and recoverable tubular shaft is further configured to be self-retractable to an unexpanded state when the positionable medical device is removed.

6. The sheath of claim 1, wherein the expandable and recoverable tubular shaft is mechanically expandable or self-expandable.

7. The sheath of claim 1, wherein the expandable and recoverable tubular shaft is slit-less.

8. The sheath of claim 1, wherein the expandable and recoverable tubular shaft comprises at least two expandable mesh layers.

9. The sheath of claim 1, further comprising a holding layer disposed along a length of the expandable and recoverable tubular shaft.

10. The sheath of claim 1, wherein the sealing layer is disposed along a proximal portion of the expandable and recoverable tubular shaft, and a distal portion of the expandable and recoverable tubular shaft is free of the sealing layer.

11. The sheath of claim 1, wherein the expandable and recoverable tubular shaft further includes an elastic, impermeable coating applied to the expandable mesh layer.

12. The sheath of claim 1, wherein the sealing layer is disposed along an interior face of the expandable mesh layer.

13. An introducer sheath comprising:
   (a) a tubular shaft comprising an expandable and recoverable mesh layer, the shaft comprising:
      (i) a lumen sized and expandable to receive a positionable medical device therethrough;
      (ii) an unexpanded state; and
      (iii) an expanded state,
      wherein the tubular shaft is configured to expand to the expanded state solely at a location where the positionable medical device is positioned within the shaft and is further configured to retract to the unexpanded state when the positionable medical device is removed from the location;
   (b) a sealing layer apart from the tubular shaft and disposed along a proximal length of the tubular shaft, wherein a porosity of the sealing layer is less than a porosity of the tubular shaft; and
   (c) a proximal hub operably coupled to a proximal end of the tubular shaft.

14. The sheath of claim 13, wherein the proximal hub comprises a hemostatic seal.

15. The sheath of claim 13, wherein the tubular shaft comprises at least two expandable and recoverable mesh layers.

16. The sheath of claim 13, wherein the sheath further comprises a holding layer disposed along a length of the tubular shaft.

17. The sheath of claim 13, further comprising at least one band disposed around the tubular shaft.

18. The sheath of claim 13, further comprising a longitudinal member disposed along a length of the tubular shaft, wherein the longitudinal member comprises a longitudinal actuating member or a longitudinal structural member.

* * * * *